United States Patent
Nagae

(10) Patent No.: US 6,841,073 B2
(45) Date of Patent: Jan. 11, 2005

(54) REVERSED-PHASE LIQUID CHROMATOGRAPHY, LIQUID CHROMATOGRAPH APPARATUS, AND COLUMN

(75) Inventor: Norikazu Nagae, Seto (JP)

(73) Assignee: Nomura Chemical Co., Ltd., Seto (JP)

( * ) Notice: Subject to any disclaimer, the term of this patent is extended or adjusted under 35 U.S.C. 154(b) by 19 days.

(21) Appl. No.: 10/427,916

(22) Filed: May 2, 2003

(65) Prior Publication Data

US 2004/0112815 A1 Jun. 17, 2004

(30) Foreign Application Priority Data

Dec. 16, 2002 (JP) ........................................ 2002-364081

(51) Int. Cl.[7] .............................................. B01D 15/08
(52) U.S. Cl. ..................... 210/635; 210/656; 210/198.2
(58) Field of Search ................................ 210/635, 656, 210/198.2, 502.1

(56) References Cited

U.S. PATENT DOCUMENTS

| | | | | |
|---|---|---|---|---|
| 3,935,097 A | * | 1/1976 | Roof | 210/659 |
| 4,016,074 A | * | 4/1977 | Porter | 210/659 |
| 4,116,046 A | * | 9/1978 | Stein | 73/61.55 |
| 4,137,161 A | * | 1/1979 | Shimada et al. | 210/659 |
| 4,840,730 A | * | 6/1989 | Saxena | 210/198.2 |
| 5,169,521 A | * | 12/1992 | Oka et al. | 210/198.2 |
| 5,340,476 A | * | 8/1994 | Berger et al. | 210/198.2 |
| 6,241,891 B1 | | 6/2001 | Nagae | 210/635 |
| 6,318,157 B1 | * | 11/2001 | Corso et al. | 73/61.52 |
| 6,627,075 B1 | * | 9/2003 | Weissgerber et al. | 210/198.2 |
| 6,632,353 B2 | * | 10/2003 | Berger et al. | 210/198.2 |

FOREIGN PATENT DOCUMENTS

| JP | A 2000-193648 | 7/2000 | 210/635 |
|---|---|---|---|
| JP | A 2002-14086 | 1/2002 | 210/635 |

* cited by examiner

Primary Examiner—Ernest G. Therkorn
(74) Attorney, Agent, or Firm—Oliff & Berridge, PLC

(57) ABSTRACT

A reversed-phase liquid chromatography using a mobile phase containing water as a main component thereof, wherein in a measurement after a flow of the mobile phase through a column is temporarily stopped and then the flow is resumed, a back pressure is applied to an outlet of the column by a back-pressure applying device which is provided between the outlet of the column and a detector.

17 Claims, 10 Drawing Sheets

REVERSED-PHASE LIQUID CHROMATOGRAPHY, LIQUID CHROMATOGRAPH APPARATUS, AND COLUMN

BACKGROUND OF THE INVENTION

1. Field of the Invention

The present invention relates to a reversed-phase liquid chromatography using a mobile phase containing water as its main component; and a liquid chromatograph apparatus and a column each for use in a reversed-phase liquid chromatography.

2. Related Art Statement

There is known a reversed-phase liquid chromatography for separating a water-soluble compound, using a mobile phase as a solvent that solves a sample to be separated, and a stationary phase as a liquid or a solid that is carried by a packing material (i.e., a carrier) that packs a column. The mobile phase contains water as its main component, and the stationary phase contains a compound having a carbon chain. Here, the mobile phase containing water as its main component is defined as encompassing a 100% water; a buffer that is prepared by adding an agent to water (hereinafter, in the present specification, the term "100% water" is defined as encompassing the buffer, unless otherwise specified); a solution that is prepared by adding, to the 100% water, a salt, an acid, etc. (e.g., sodium phosphate, trifluoroacetic acid, triethylamine, or sodium perchlorate); or a mixture of the 100% water or the solution and a from 1% to 5% organic solvent (e.g., acetonitrile).

In the case where a mobile phase containing water as its main component is used with a reversed-phase stationary phase to which an alkyl group having from 8 to 18 carbons is bonded, that is widely used as a stationary phase for a reversed-phase liquid chromatography, there are known those facts that time of retention of sample is not stable and the retention time decreases as the time in which the mobile phase is flowed increases, that is, that reproducibility of the retention time is low. In particular, in the case where the flow of the mobile phase is resumed after it is temporarily stopped, it is known that the retention time significantly decreases (see FIGS. 2, 3, and 5 shown in Patent Document 1 (i.e., Japanese Laid-Open Patent Document No. 2002-14086)). Since, in the chromatography, the compound separated is identified based on the retention time, the mobile phase cannot be used with the stationary phase if the reproducibility of retention time is low.

Conventionally, it has been speculated that the reason why the reproducibility of retention time is low is that when the mobile phase containing water as its main component is flowed through the stationary phase, the carbon chains gradually collapse due to their hydrophobicity and so-called "slipping" occurs, that is, the interaction between the stationary phase and the solute decreases. In order to solve the problem that the retention time decreases as the time increases, there are some cases where a column packing material having a stationary phase including a polar group, a column packing material having a stationary phase whose hydophobicity is lowered by decreasing the density of alkyl group, or a column packing material having a stationary phase that does not physically collapse, such as trimethylsilyl group, is used. The packing material having the stationary phase including the polar group may be a packing material including, as a stationary phase, a compound having a carbon chain and a high-polar group, such as amide group or carbamate group, bonded to the carbon chain, the stationary phase being bonded to a carrier (silica, polymer, etc.); or a packing material including stearyl group (its carbon number is 18) that is widely used as a hydrocarbon stationary phase, the stearyl group being bonded to a silica carrier, the residual silanol groups present on the silica carrier being decreased using a polar group as an endcapping.

In the above-described background, the Inventor had elucidated that, contrary to a conclusion expected from the above-explained slipping, the water-100 mobile phase can be used with a stationary phase including an alkyl group having a long carbon chain (whose carbon number is, e.g., 30) (see Patent Document 2 (i.e., Japanese Laid-Open Patent Document No. 2000-193648 or its corresponding U.S. Pat. No. 6,241,891)).

In addition, the Inventor had proved that, in the case where the pore diameter of a packing material carrying a stationary phase is large, or temperature is kept low, a mobile phase containing water as its main component can be used with either a stationary phase including an alkyl group having a long carbon chain or a stationary phase including an alkyl group having a short carbon chain whose carbon number is not greater than 22 (see the above-indicated Patent Document 1).

Thus, in the reversed-phase liquid chromatography in which the mobile phase containing water as its component is used, it is needed to use a column that is packed with a specific stationary phase usable with the mobile phase, or keep temperature low. However, since keeping the temperature low needs a cooling device, an additional expense is needed. In addition, the cost of each measurement is increased. Meanwhile, in the case where the temperature is not kept low, it is needed to use a column that is packed with a specific stationary phase, and accordingly a common reversed-phase column that is widely used in a reversed-phase liquid chromatography, such as a column packed with octadecyl group (whose carbon number is 18) that is most widely used, cannot be used because the common column has a high hydrophobicity.

SUMMARY OF THE INVENTION

It is therefore an object of the present invention to provide an a reversed-phase liquid chromatography in which a mobile phase containing water as its main component can be used with any sort of column, and a liquid chromatograph apparatus and a column each for use in that reversed-phase liquid chromatography.

The Inventor has carried out extensive studies and found that even in the case where a measurement is performed in the manner that the flow of a mobile phase is resumed after it is temporarily stopped, the degree of decrease in the retention time can be lowered by adding a high back pressure to an outlet of a column, and that the decrease in the retention time can be substantially avoided by adding, to the outlet of the column, a back pressure higher than a reference value. In addition, the Inventor has found that the high back pressure is particularly needed at an initial time when the flow is resumed and that after the initial time, the decrease in the retention time can be lowered by adding a back pressure lower than the initial back pressure. The present invention has been developed based on these findings.

The above object has been achieved by the present invention. According to a first aspect of the present invention, there is provided a reversed-phase liquid chromatography using a mobile phase containing water as a main component thereof, wherein, in a measurement after a flow of the mobile phase through a column is temporarily stopped and then the flow is resumed, a back pressure is applied to an outlet of the column by a back-pressure applying device which is provided between the outlet of the column and a detector.

Even in the measurement after the flow of the mobile phase is temporarily stopped and then the flow is resumed, if the back pressure is applied to the outlet of the column, the decrease in the retention time can be reduced and accordingly the mobile phase containing water as the main component thereof can be used. In addition, since the back pressure is applied to the outlet of the column by the back-pressure applying device provided between the outlet of the column and the detector, the back pressure is not applied to the detector and accordingly it is not needed to take into account what degree of pressure the detector can resist.

According to a second aspect of the present invention, there is provided a reversed-phase liquid chromatography using a mobile phase containing water as a main component thereof, wherein, in a measurement after a flow of the mobile phase through a column is temporarily stopped and then the flow is resumed, a back pressure not lower than 5 MPa is applied to an outlet of the column.

Even in the measurement after the flow of the mobile phase is temporarily stopped and then the flow is resumed, if the back pressure not lower than 5 MPa is applied to the outlet of the column, the decrease in the retention time can be reduced and accordingly the mobile phase containing water as the main component thereof can be used. There have been some cases where a back pressure is applied to a downstream side of a detector so as to prevent air bubbles from entering the detector or prevent generation of air bubbles and consequently some back pressure is applied to the outlet of the column. However, the back pressure is at the level of from 1 to 3 MPa at the highest that cannot significantly reduce the decrease in the retention time.

According to a third aspect of the present invention, there is provided a reversed-phase liquid chromatography using a mobile phase containing water as a main component thereof, wherein, in a measurement after a flow of the mobile phase through a column is temporarily stopped and then the flow is resumed, an initial back pressure not lower than 5 MPa is applied to an outlet of the column when the flow is resumed; and a back pressure lower than the initial back pressure is applied to the outlet of the column after a sample is put in the column.

Even in the measurement after the flow of the mobile phase is temporarily stopped and then the flow is resumed, if the initial back pressure not lower than 5 MPa is applied to the outlet of the column when the flow is resumed and the back pressure lower than the initial back pressure but higher than zero is continuously applied to the outlet of the column after the sample is put, the decrease in the retention time can be reduced and accordingly the mobile phase containing water as the main component thereof can be used. In addition, since the back pressure applied to the outlet of the column after the sample is put is lower than the initial back pressure applied when the flow is resumed, the load applied to the column or a liquid chromatograph apparatus including the column. Thus, the lifetime of the column or the apparatus can be increased.

According to the second or third aspect of the present invention, a location where the back pressure is applied may be a location on a downstream side of a detector or a location between the outlet of the column and the detector. However, since a pressure that a common detector can resist is not so high, it is preferred that the back pressure be applied to the outlet of the column by a back-pressure applying device which is provided between the column and a detector.

The mobile phase used according to each of the first to third aspects of the present invention may be any of the above-described mobile phases each containing water as its main component. In the conventional technique, the 100%-water mobile phase suffers from the problem that the retention time is largely reduced. In contrast, according to the present invention, the mobile phase containing 100% of water can be preferably used. In addition, there is no limitation to the stationary phase. For example, a hydrocarbon group having a high hydrophobicity or a carbon chain to which amide group is bonded may be used as the stationary phase. The hydrocarbon group may be a straight-chain alkyl group, a branched-chain alkyl group, or a hydrocarbon group having a phenyl group in its main or side chain.

Also, there is no limitation to a packing material that packs the column used according to any of the first to third aspects of the present invention. However, as disclosed in the above-indicated Patent Document 1, in the case where the pore diameter of the packing material to which the stationary phase is bonded is not smaller than a reference value, the retention time does not decrease so much even if no back pressure may be applied to the outlet of the column. Therefore, each of the first to third aspects of the present invention is advantageous to such a reversed-phase liquid chromatography in which a packing material described as unusable in Patent Document 1 is used. That is, each of the first to third aspects of the present invention is advantageous if a packing material which packs the column satisfies following expressions:

$y<1.83x+8.17$ ($1 \leq x \leq 8$, $y \leq 100$)

$y<-0.33x+25.4$ ($8 \leq x \leq 18$, $y \leq 100$)

$y<-0.93x+36.2$ ($18 \leq x \leq 30$, $y \leq 100$)

where x is an alkyl-group-equivalent main-chain carbon number of a stationary phase, and
y is a pore diameter (nm) of the packing material carrying the stationary phase.

The alkyl-group-equivalent main-chain carbon number is defined as a carbon number of a main chain of a stationary phase that is counted according to the manner in which if the main chain includes a phenyl group, then the carbon number of the phenyl group is counted as 3, and other carbons are counted as they are.

It is preferred that the back pressure applied to the outlet of the column be higher as the pore diameter of the packing material of the column is smaller. For example, it is preferred that a packing material which packs the column have, in a state in which the packing material carries the stationary phase, a not less than 10 nm diameter, and that an initial back pressure not lower than 15 MPa be applied to the outlet of the column when the flow is resumed, and it is also preferred that a packing material which packs the column have, in a state in which the packing material carries the stationary phase, a not less than 8 nm diameter, and that an initial back pressure not lower than 20 MPa be applied to the outlet of the column when the flow is resumed.

According to a fourth aspect of the present invention, there is provided a liquid chromatograph apparatus that is advantageously used in the reversed-phase liquid chromatography according to any of the first to third aspects of the present invention. According to the fourth aspect, a back-pressure applying device applies a back pressure to an outlet of a column and is provided in a connecting pipe which connects between the column and a detector.

In the liquid chromatograph apparatus, the back-pressure applying device is provided in the connecting pipe which connects between the column and the detector, and accordingly no back pressure is applied from the back-pressure applying device to the detector. Therefore, the detector is not required to have a pressure resistance.

The structure of a column itself can be utilized to apply a back pressure to the column. More specifically described, according to a fifth aspect of the present invention, there is provided a column for use in a reversed-phase liquid chromatography using a mobile phase containing water as a main component thereof, wherein a tube is provided on a downstream side of a separating portion of the column that is packed with a packing material, and has an inner diameter not greater than one twentieth of an inner diameter of the separating portion. According to the fifth aspect of the present invention, the tube provided downstream of the separating portion provides a resistance to the flow and thereby applies a back pressure to the separating portion.

According to a sixth aspect of the present invention, there is provided a column system for use in a reversed-phase liquid chromatography using a mobile phase containing water as a main component thereof, wherein a back-pressure applying column is provided on a downstream side of a separating column that is packed with a first packing material and has a first inner diameter, is packed with a second packing material, and has a second inner diameter, wherein at least one of a particle diameter of the second packing material and the second inner diameter is smaller than a corresponding one of a particle diameter of the first packing material and the first inner diameter. According to the sixth aspect of the present invention, the back-pressure applying column provides a resistance to the flow and thereby applies a back pressure to the separating column. According to each of the fifth and sixth aspects of the present invention, the structure of a column or columns is utilized to apply a back pressure to an outlet of the column or columns, and accordingly the mobile phase containing water as its main component can be used by just attaching the column or columns to a common liquid chromatograph apparatus.

BRIEF DESCRIPTION OF THE DRAWINGS

The above and optional objects, features, and advantages of the present invention will be better understood by reading the following detailed description of preferred embodiments of the invention when considered in conjunction with the drawings, in which.

DETAILED DESCRIPTION OF PREFERRED EMBODIMENTS

Figure 1:
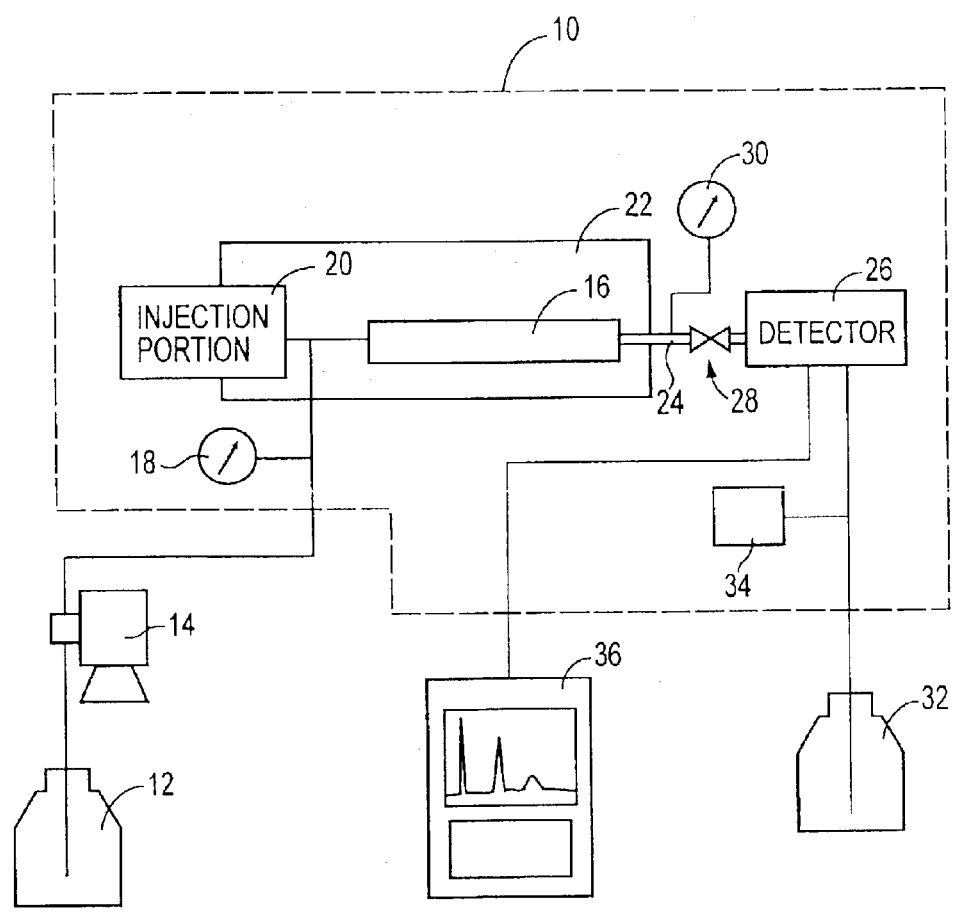
FIG. 1 is a view for explaining a construction of an arrangement for carrying out a reversed-phase liquid chromatography to which the present invention is applied, the arrangement including a high performance liquid chromatograph apparatus to which the present invention is also applied.

Hereinafter, there will be described a preferred embodiment of the present invention by reference to the drawings. FIG. 1 is a view for explaining an arrangement for carrying out a reversed-phase liquid chromatography. This arrangement includes a high performance liquid chromatograph apparatus 10. The present invention is applied to the reversed-phase liquid chromatography, the high performance liquid chromatograph apparatus 10, and a column 16 which is usable with the chromatograph apparatus 10.

As shown in FIG. 1, a mobile-phase solvent (i.e., a separating liquid) that is stored, in advance, as a mobile phase in a solvent tank 12, is introduced into a column 16, by a pump 14, at a pre-set rate, e.g., 1.0 ml/min. The mobile-phase solvent is a solvent that contains water as its main component, for example, a 100% water. A pressure gauge 18 measures a pressure at an inlet of the column 16. In an injection portion 20, there is provided an injector, not shown, that is used to inject a sample, solved in water, into the column 16.

The column 16 is not part of the high performance liquid chromatograph apparatus 10, and a column suitable for the sample to be separated, is selected and disposed in a column oven 22 of the chromatograph apparatus 10. The column 16 is, for example, a stainless-steel tube, and may be selected from various sorts of columns having different inner diameters and different lengths, such as a 4.6-mm-inner-diameter and 150-mm-length general-purpose analysis column, a 1 to 2 mm inner diameter analysis column (called "semi-micro column"), or a 20-mm-inner-diameter and 250-mm-length separation column. The column 16 is packed with a packing material as a carrier which carries, in advance, a stationary phase. The carrier is, for example, silica (i.e., silica gel), and the stationary phase is bonded, in advance, to the silanol groups present on the surface of the carrier.

A connecting pipe 24 is connected, at its one end, to an outlet of the column 16. The other end of the connecting pipe 24 is introduced into a detector 26. A pipe having an inner diameter suitable for that of the column 16 is selected as the connecting pipe 24. For example, in the case where a column 16 having a 4.6 mm inner diameter is used, a connecting pipe 24 having, e.g., a 0.13 mm inner diameter is used. The connecting pipe 24 may have a length of, e.g., from 50 cm to 3 m.

The high performance liquid chromatograph apparatus 10, shown in FIG. 1, includes a control valve 28 functioning as a back-pressure applying device. The control valve 28 is provided in an intermediate portion of the connecting pipe 24. The control valve 28 is for applying or adding a back pressure to the outlet of the column 16. The control valve 28 is, for example, a pressure control valve such as a pressure reducing valve, or a flow control valve such as a throttle valve. The back pressure added by the control valve 28 to the outlet of the column 16 is measured by a pressure gauge 30 that is connected to a portion of the connecting pipe 24 that is located on an upstream side of the control valve 28.

The sample injected from the injection portion 18 is separated by the column 16 and is introduced into the detector 26. The detector 26 is, for example, a UV detector or a differential refractometer for detecting the sample. An eluant (i.e., the mobile phase) that has passed through the detector 26 is collected in a waste liquid tank 32. A flow meter 34 is connected to a pipe connecting between the detector 26 and the waste liquid tank 32. Results obtained by the detector 26 are recorded by a recording device 36 that also has the function of processing data.

Next, there will be described the finding that the decrease in the retention time can be reduced by adding the back pressure to the outlet of the column 16 when the pump 14 is temporarily stopped and subsequently the flow of the mobile phase through the column 16 is resumed to do measurements.

Figure 2:
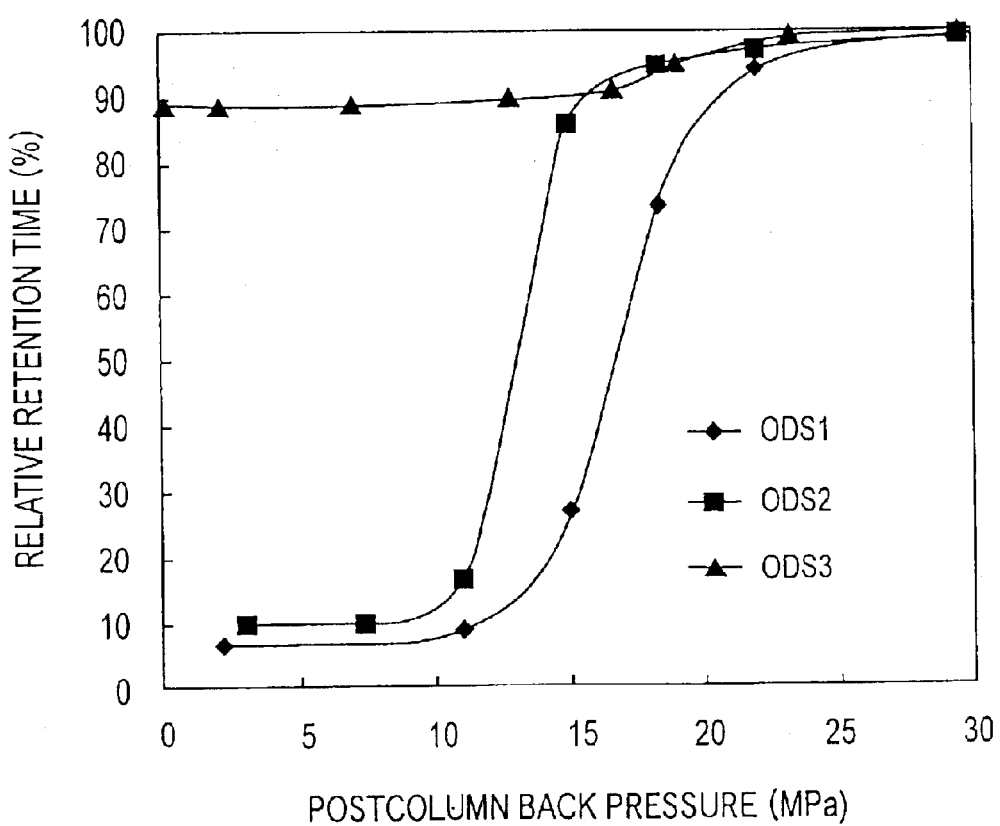
FIG. 2 is a view showing results of an experiment in which a relative retention time (%) is measured each time a pump is stopped and then flow of a mobile phase is resumed, while a postcolumn back pressure is changed.

FIG. 2 is a graph showing experimental results obtained by measuring relative retention times (%) as the back pressure added to the outlet of the column 16 is gradually changed each time the pump 14 is temporarily stopped and then the flow of the mobile phase through the column 16 is resumed.

The experiment was carried out under the following conditions:
Column dimensions: 4.6 mm inner diameter×150 mm length
Pressure at inlet of column: pressure equal to pressure at outlet of column plus 7 MPa
Packing material: silica carrying octadecylsilyl groups
Particle diameter of packing material: 5 μm
Other characteristics of packing material and stationary phase: see TABLE 1
Mobile phase: 100% water (containing no agents for use in preparing a buffer)
Flow rate: 1.0 ml/min
Temperature: 40° C.
Detector: differential refractometer
Sample: 2-propanol

TABLE 1

|  | ODS1 | ODS2 | ODS3 |
|---|---|---|---|
| Stationary phase | ODS*1 | ODS | ODS |
| Denstiy of ODS (μmol/m²) | 3.0 | 3.2 | 1.6 (TMS*2 2.3) |
| Carbon content (%) | 20 | 18 | 15 |
| Surface area of packing material (m²/g) | 350 | 300 | 450 |
| Pore diameter (nm) of packing material carrying stationary phase | 8.6 | 10.3 | 7.6 |
| Endcapping | each bonded with TMS twice | | |

*1ODS means octadecyl groups.
*2TMS means trimethylsilyl groups.

The flow of the mobile phase through the column 16 is stopped and resumed as follows: First, the column 16 is flushed with a mixture of acetonitrile and water (7:3) for one hour, and then, in a state in which the back pressure after the column 16 is 30 MPa, the content of the water is gradually increased and eventually the mixture is replaced with a 100%-water mobile phase. The relative retention times, shown in FIG. 2, are calculated using, as 100%, a time of retention of each sample that was obtained in a measurement carried out immediately after the replacement with the 100% water finished. After this measurement was carried out, the pump 14 is stopped for one hour and, subsequently, in a state in which each selected back pressure is added to the outlet of the column 16, the 100%-water mobile phase is flowed through the column 16. After one hour, each sample is injected again into the column 16 to measure a retention time.

As shown in FIG. 2, in the case where ODS1 or ODS2 is used as the stationary phase, the retention time significantly decreases if, after the stopping of the pump 14, the flow of the mobile phase is resumed without an appropriate back pressure being added to the outlet of the column 16, like in the conventional manner. The reason why the retention time significantly decreases is that the mobile phase is expelled from the pores of the packing material, as discussed in the above-indicated Patent Document 1.

However, in the case where ODS1 is used as the stationary phase, the relative retention time significantly increases when the back pressure is equal to from 12 MPa to 18 MPa, and reaches about 90% when the back pressure is equal to 20 MPa. Thus, it can be concluded that ODS1 can be used if the back pressure is not smaller than 20 MPa. In addition, in the case where ODS2 is used as the stationary phase, the relative retention time significantly increases when the back pressure is equal to from 11 MPa to 14 MPa, and reaches about 90% when the back pressure is equal to 15 MPa. Thus, it can be concluded that ODS2 can be used if the back pressure is not smaller than 15 MPa.

As explained above, the reason why the retention time decreases is that the mobile phase is expelled from the pores of the packing material. Therefore, the reason why the decrease in the retention time can be reduced by adding the appropriate back pressure after the column 16 is that the mobile phase expelled from the pores of the packing material is again forced into the pores by the back pressure added after the column 16. When the physical characteristics of ODS1 are compared with those of ODS2, a substantial difference between them is only a difference between the respective pore diameters of the respective packing materials in the state in which the packing materials carry the respective stationary phases. Therefore, an appropriate back pressure added after the column 16 so as to obtain a sufficiently high reproducibility depends on the pore diameter of packing material. The smaller the pore diameter of the packing material carrying the stationary phase is, the higher back pressure is needed.

In ODS1 or ODS2, the stationary phase bonded to the packing material contains only the octadecyl groups. In contrast, in ODS3, the density of the octadecyl groups is decreased, and the trimethylsilyl groups are bonded to the packing material. Since the trimethylsilyl groups have a high hydrogen-bonding capacity, the retention time of ODS3 is not decreased so much even if it is used with the 100%-water mobile phase. However, as shown in FIG. 2, if, after the stopping of the pump 14, the flow of the mobile phase is resumed with no back pressure being added after the column 16, like in the conventional manner, the retention time decreases by about 10%. In addition, as shown in FIG. 2, the retention time of ODS3 increases when the back pressure is equal to from 17 MPa to 20 MPa. Thus, it can be concluded that, irrespective of the amount of decrease of the retention time, the back pressure added after the column 16 so as to recover the retention time depends on the pore diameter of the packing material to which the stationary phase has been bonded.

Figure 3:
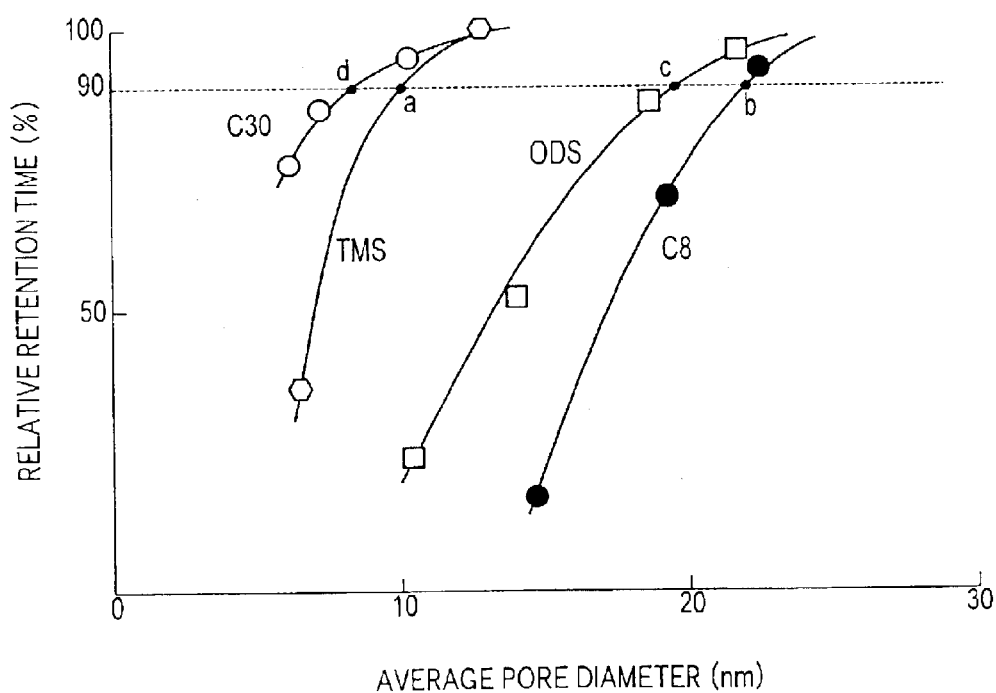
FIG. 3 is a view showing results of an experiment in which various sorts of packing materials having different average pore diameters in respective states in which the packing materials are bonded with respective stationary phases, are synthesized, and a relationship between average pore diameter and relative retention time is determined.
Figure 4:
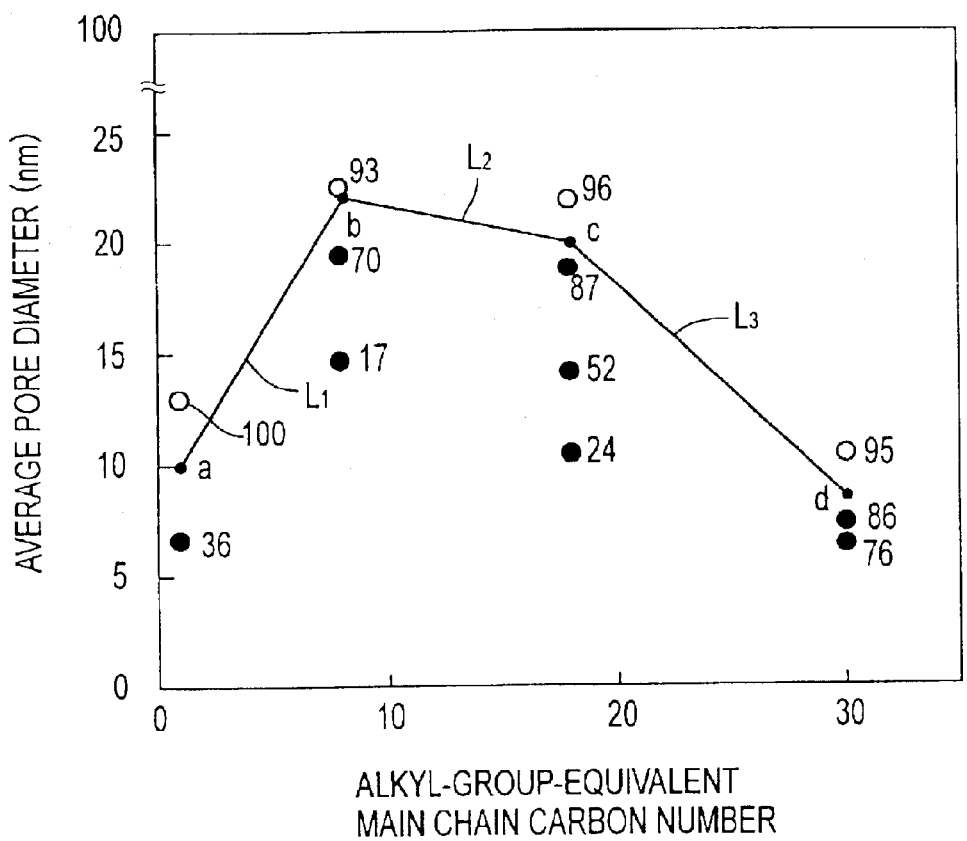
FIG. 4 is a graph showing the data points and the four intersection points a, b, c, d, all shown in FIG. 3, that are re-plotted in a two-dimensional coordinate system defined by an axis of alkyl-group-equivalent main chain carbon number and an axis of average pore diameter.

Next, there will be explained, by reference to FIGS. 3 and 4, an experiment that was carried out to determine an appropriate range of pore diameter of packing material that is particularly effective in reducing the decrease of retention time by increasing the back pressure after the column 16. FIGS. 3 and 4 are also disclosed in the above-indicated Patent Document 1.

FIG. 3 shows results obtained from the experiment in which various sorts of packing materials that have different average pore diameters in the state in which those packing materials are bonded with respective stationary phases were synthesized and a relationship between average pore diameter and relative retention time was determined. The experiment was carried out under the following conditions:
Column dimensions: 4.6 mm inner diameter×150 mm length
Stationary phase: triacontyl groups (C30) octadecyl groups (ODS) octyl groups (C8) trimethylsilyl groups (TMS)
Mobile phase: 10 mmol/l sodium phosphate (pH 7.0)
Flow rate: 1.0 ml/min
Temperature: 40° C.
Detector: UV 254 nm
Sample: thymine
Postcolumn back pressure: not added In this experiment, the synthesis of each packing material was carried out under a no-water condition in which a very excessive amount of agent corresponding to each stationary phase was added, and accordingly each packing material was bonded with a high density of stationary phase. In addition, each of the three packing materials that have, as their stationary phases, the triacontyl groups, the octadecyl groups, and the octyl groups, respectively, was bonded with the trimethylsilyl groups as an endcapping, so as to reduce the residual silanol groups. Relative retention times, shown in FIG. 3, were calculated as follows: First, a retention time measured immediately after the contents of pores of each packing material were replaced with the 100%-water mobile phase, i.e., measured one hour after the sodium-phosphate mobile phase was replaced with the 100%-water mobile phase, was determined as a standard retention time. Then, a retention time is measured one hour after the flow of the mobile phase through each packing material was stopped for twelve hours and then the flow is resumed, and a relative value of the thus measured retention time relative to the standard retention time was determined as a relative retention time of the each packing material. As discussed in Patent Document 1, the retention time does not substantially decrease after the flow of the mobile phase was stopped for more than ten hours. Therefore, it can be said that the retention time measured one hour after the flow of the mobile phase was stopped for twelve hours and then the flow is resumed, is the most decreased retention time.

FIG. 3 shows four intersection points, a, b, c, and d, where four curves each of which connects the respective relative retention times measured for a corresponding one of the four stationary phases, intersect a line representing a 90% relative retention time. FIG. 4 is a graph showing all the data points and the four intersection points a, b, c, d, shown in FIG. 3, that are re-plotted in a two-dimensional coordinate system defined by an axis of alkyl-group-equivalent main-chain carbon number and an axis of average pore diameter. In FIG. 4, each of the data points is accompanied by a percentage value indicating a corresponding measured relative retention time. In FIG. 4, a segment $L_1$ connects between the points a, b; a segment $L_2$ connects between the points b, c; and a segment $L_3$ connects between the points c, d. Assuming that x is an alkyl-group-equivalent main-chain carbon number and y is an average pore diameter (nm), the segments $L_1$, $L_2$, $L_3$ are represented by the following expressions (1), (2), (3), respectively:

$$\text{Segment } L_1: y=1.83x+8.17 \ (1 \leq x \leq 8) \tag{1}$$

$$\text{Segment } L_2: y=-0.33x+25.4 \ (8 \leq x \leq 18) \tag{2}$$

$$\text{Segment } L_3: y=-0.93x+36.2 \ (18 \leq x \leq 30) \tag{3}$$

The points a, b, c, d represent the respective 90% relative retention times, and the segments $L_1$, $L_2$, $L_3$ connect those points a, b, c, d with each other. Therefore, each packing material whose alkyl-group-equivalent main-chain carbon number and average pore diameter are located above the segments $L_1$, $L_2$, $L_3$ shown in FIG. 4, exhibits a not smaller than 90% relative retention time and accordingly it can be used with the 100%-water mobile phase without a back pressure after the column 16. Thus, it is significantly needed to add a postcolumn back pressure to such a packing material whose alkyl-group-equivalent main-chain carbon number and average pore diameter are located below the segments $L_1$, $L_2$, $L_3$ shown in FIG. 4, that is, satisfy the following expressions (4), (5), (6):

$$y<1.83x+8.17 \ (1 \leq x \leq 8) \tag{4}$$

$$y<-0.33x+25.4 \ (8 \leq x \leq 18) \tag{5}$$

$$y<-0.93x+36.2 \ (18 \leq x \leq 30) \tag{6}$$

Next, there will be described the finding that if the initial back pressure added when the flow of the mobile phase is resumed after the stopping of the flow is sufficiently high, the decrease of retention time can be reduced even if a back pressure lower than. the initial back pressure is added after the injection of sample.

Figure 5:
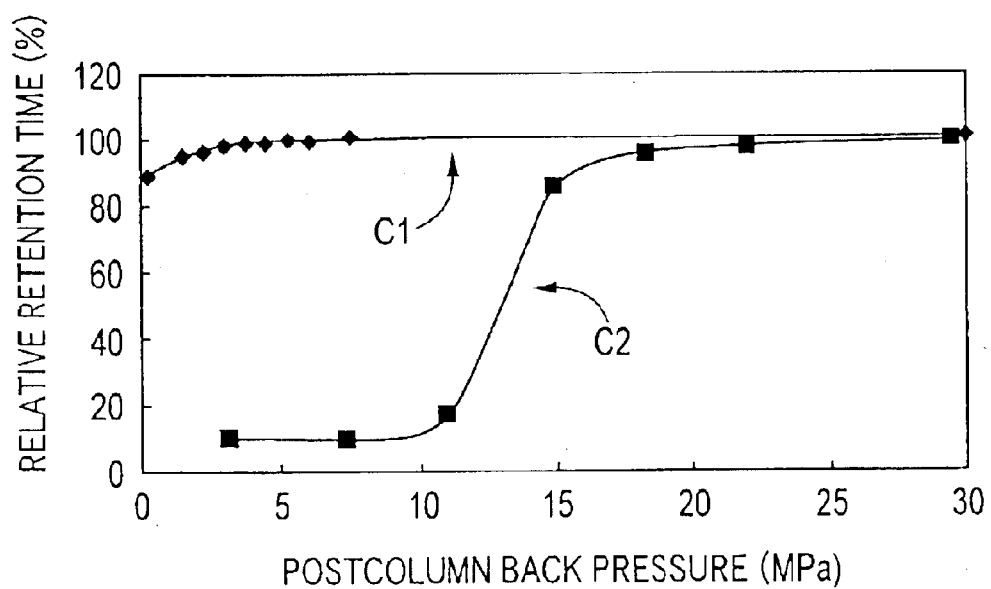
FIG. 5 is a view showing results of an experiment in which a relative retention time is measured each time a postcolumn back pressure when flow of a mobile phase is resumed is made equal to 30 MPa and then the back pressure is lowered without stopping the flow of the mobile phase.

In FIG. 5, a curve C1 represents results obtained by measuring respective relative retention times (%) when a 30 MPa postcolumn back pressure (i.e., initial back pressure) is added when the flow of the mobile phase is resumed and then the back pressure is gradually lowered without stopping of the flow of the mobile phase; and a curve C2, i.e., the curve of ODS2 shown in FIG. 2 is shown for comparison with the curve C1.

The experimental conditions under which the curve C1 was obtained are the same as those under which the curve of ODS2 shown in FIG. 2 was obtained, except for the conditions under which the mobile phase was flowed through the column. The relative retention times represented by the curve C1 are calculated using, as 100%, the retention time measured when the postcolumn back pressure was 30 MPa. Thus, each relative retention time represented by the curve C1 and each relative retention time shown in FIG. 2 are defined in different manners. However, as will be described later, it can be said that both of those relative retention times are defined in the same manner. The conditions under which the mobile phase was flowed through the column to obtain the curve C1 are as follows: First, in a state in which the postcolumn back pressure is 30 MPa, the 100%-water mobile phase is flowed for several minutes. Subsequently, while the flowing of the mobile phase is continued, the back pressure is lowered to each of respective pressure values shown in FIG. 5 or TABLE 2. After the flowing of the mobile phase is further continued for one hour, a retention time is measured. As shown in FIG. 2, if the postcolumn back pressure is 30 MPa, the measured retention time is substantially the same as the retention time measured immediately after the mixture mobile phase is replaced with the 100%-water mobile phase. Therefore, each relative retention time shown in FIG. 5 has substantially the same meaning as that of each relative retention time shown in FIG. 2. Thus, it can be said that each relative retention time shown in FIG. 5 is a value relative to the retention time measured immediately after the mixture mobile phase is replaced with the 100%-water mobile phase.

According to the present experiment, in the state in which the initial postcolumn back pressure is 30 MPa, the mobile phase is flowed through the column for several minutes, for the purpose of taking the precaution of keeping the high back pressure for a sufficiently long time. However, it needs only several seconds for the mobile phase to enter the pores of the packing material. In addition, in this experiment, the initial back pressure is 30 MPa. However, as shown in FIG. 2, if the back pressure is not lower than 15 MPa, the retention time can recover. Therefore, the initial back pressure may be not lower than 15 MPa (e.g., 17 MPa, 18 MPa, or 20 MPa).

TABLE 2 shows a measured value corresponding to each data point represented by the curve C1 shown in FIG. 5; and TABLE 3 shows a measured value corresponding to each data point represented by the curve C2 shown in FIG. 5.

TABLE 2

| Back Pressure (MPa) | Relative Retention Time (%) |
| --- | --- |
| 0.2 | 89.3 |
| 1.5 | 95.1 |
| 2.3 | 96.1 |
| 3 | 98.1 |
| 3.8 | 98.4 |
| 4.5 | 99 |
| 5.3 | 99.3 |
| 6.1 | 99.6 |
| 7.6 | 100 |
| 30 | 100 |

TABLE 3

| Back Pressure (MPa) | Relative Retention Time (%) |
| --- | --- |
| 3 | 10 |
| 7.38 | 10.4 |
| 11 | 16.8 |

TABLE 3-continued

| Back Pressure (MPa) | Relative Retention Time (%) |
| --- | --- |
| 15 | 86.1 |
| 18.4 | 94.9 |
| 22 | 97.2 |
| 29.5 | 99 |

The curve C2 shown in FIG. 5 and TABLE 3 prove that a good reproducibility cannot be obtained unless a high back pressure is added when the flow of the mobile phase is resumed; and FIG. 5 and TABLE 2 prove that once a high back pressure is added, the retention time does not decrease so much even if the back pressure is subsequently lowered. In a particular case where the back pressure is 0.2 MPa, the relative retention time measured after twenty hours showed a 15% decrease. On the other hand, in the case where the back pressure is 5 MPa, the relative retention time measured after twenty hours showed no change. Therefore, to what degree the back pressure can be lowered depends on the time duration in which the mobile phase is continuously flowed, and/or the desired reproducibility. However, it can be said that the back pressure can be lowered to at least 5 MPa.

Next, there will be described other sorts of back-pressure applying devices that can be used according to the present invention. In the high performance liquid chromatograph apparatus 10, the control valve 28 is used as the back-pressure applying device. However, a back-pressure applying device 38 shown in FIG. 6 may be used.

Figure 6:
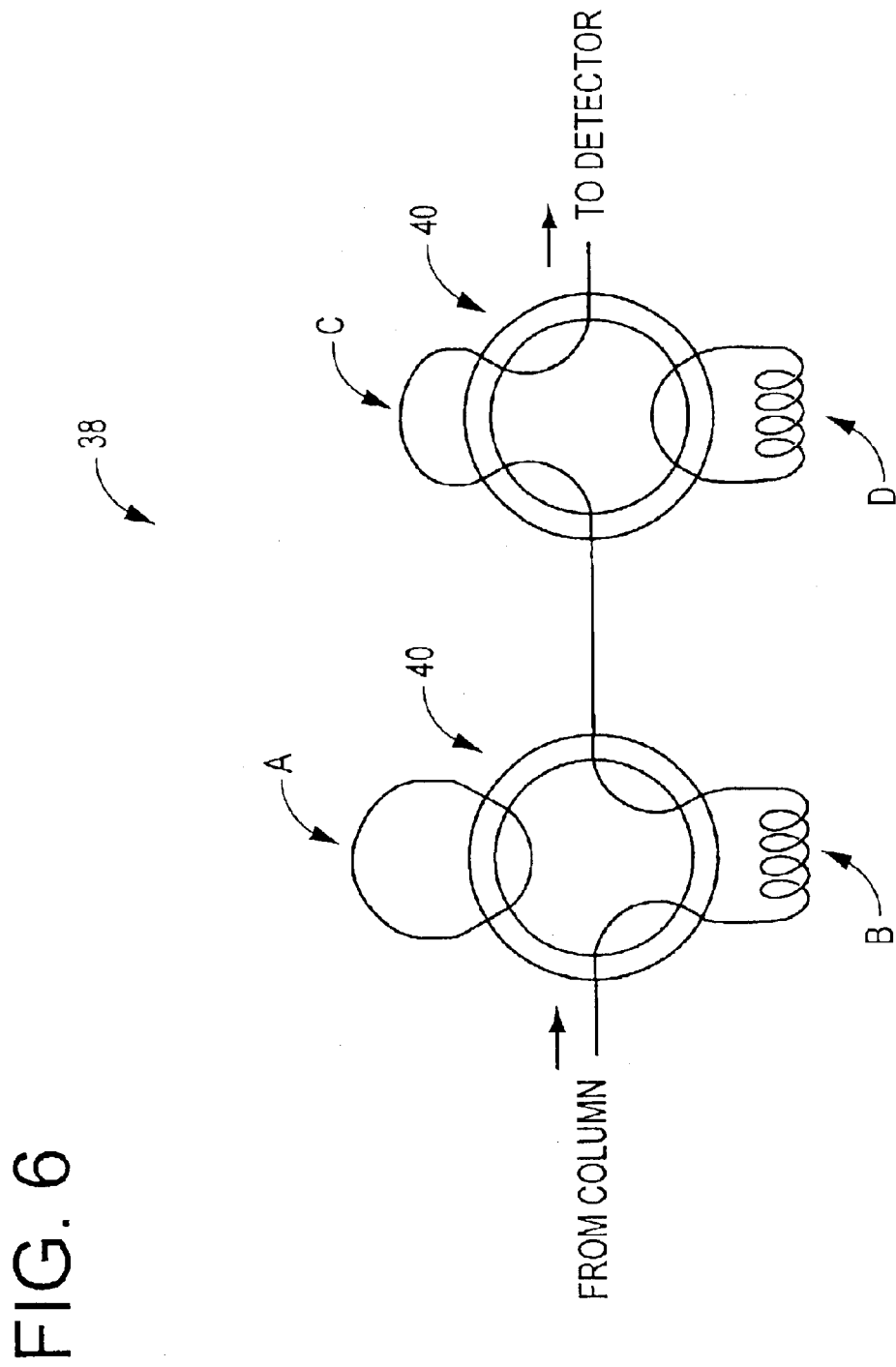
FIG. 6 is a view showing another back-pressure applying device that is different from a back-pressure applying device (i.e., a control valve) employed by the liquid chromatograph apparatus shown in FIG. 1.

The back-pressure applying device shown in FIG. 6 includes one or more six-port valves 40 (two valves 40 employed in the embodiment shown in FIG. 6), and various pipes that are connected to the six-port valves 40 and have different lengths and/or inner diameters, i.e., different flow resistances. Each of the six-port valves 40 functions as a channel-switching valve for selecting an appropriate one of a plurality of channels.

Figure 7:
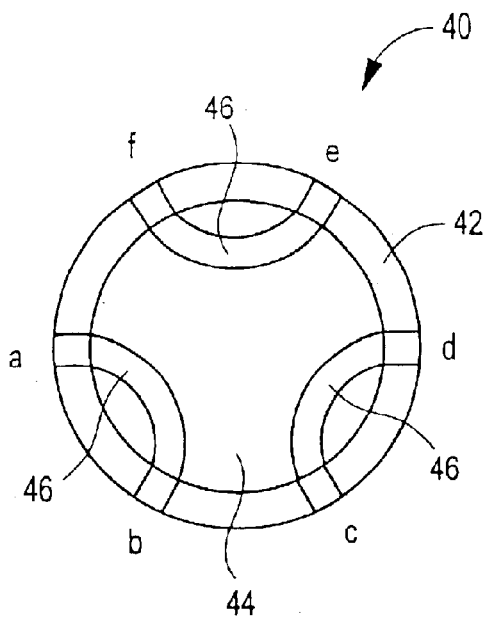
FIG. 7 is a view for explaining the structure and operation of a six-port valve employed by the back-pressure applying device of FIG. 6.
Figure 8:
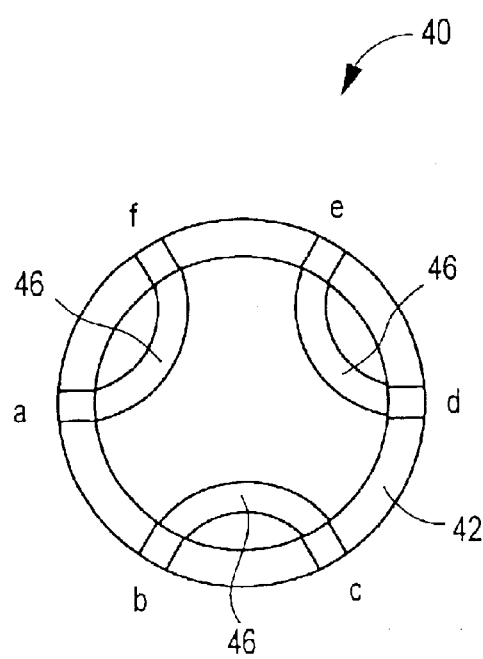
FIG. 8 is another view for explaining the structure and operation of the six-port valve employed by the back-pressure applying device of FIG. 6.

FIGS. 7 and 8 are views for explaining the structure and operation of each six-port valve 40. The six-port valve 40 includes a housing 42 having six ports a, b, c, d, e, f to which the pipes are connected, and a rotary valve member 44 that is accommodated in the housing 42 such that the valve member 44 is rotatable relative to the housing 42. The rotary valve member 44 has three channels 46 each of which can connect between two ports adjacent to each other. When the valve member 44 is rotated, the six-port valve 40 is switchable between a first position, shown in FIG. 7, in which the ports a, b are connected to each other, the ports c, d are connected to each other, and the ports e, f are connected to each other, and a second position, shown in FIG. 8, in which the ports a, f are connected to each other, the ports b, c are connected to each other, and the ports d, e are connected to each other.

Therefore, the back-pressure applying device 38 shown in FIG. 6, can select each one of four passages, i.e., a first passage including pipes A, C, a second passage including pipes A, D, a third passage including pipes B, C, and a fourth passage including pipes B, D. For example, in the case where the pipe A can apply a 5 MPa back pressure, the pipe B can apply a 15 MPa back pressure, the pipe C can apply a 1 MPa back pressure, and the pipe D can apply a 15 MPa back pressure, the fourth passage including the pipes B, D can apply a 30 MPa back pressure, the second passage including the pipes A, D can apply a 20 MPa back pressure, the third passage including the pipes B, C can apply a 16 MPa back pressure, and the first passage including the pipes A, C can apply a 6 MPa back pressure. Since the back-pressure applying device 38 can apply different back pressures, it can be advantageously used in the measuring method in which the initial back pressure applied when the flow of the mobile phase is resumed is high and the back pressure is lowered after the injection of sample.

Figure 9:
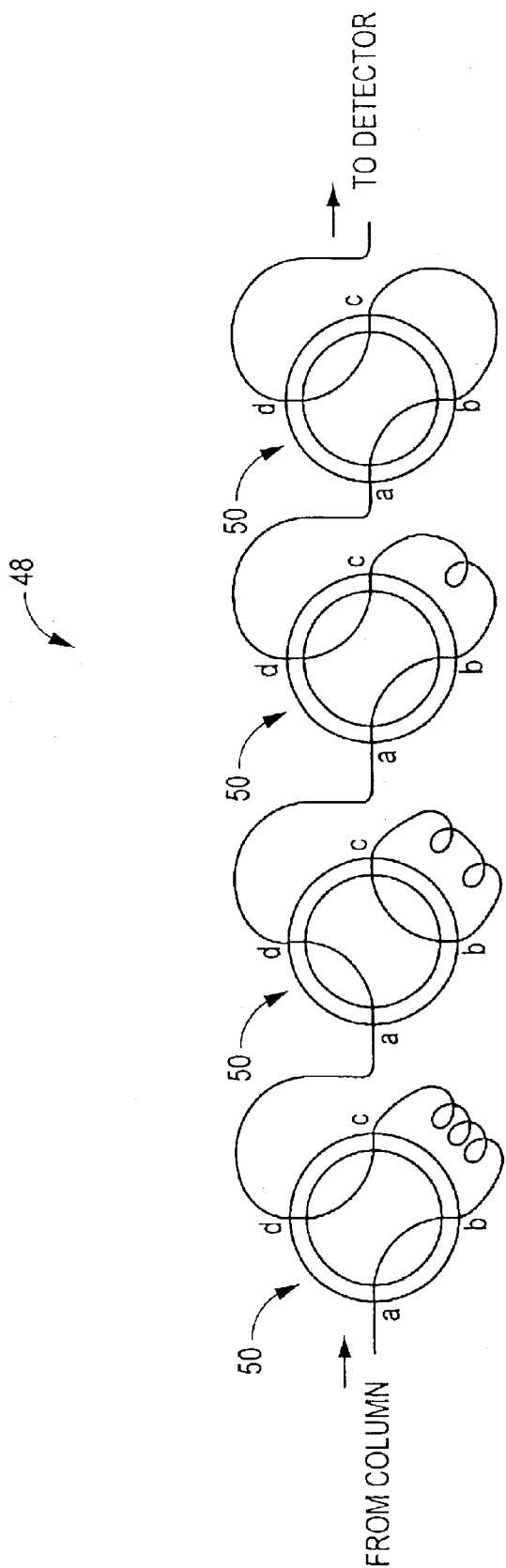
FIG. 9 is a view showing another back-pressure applying device that is different from the back-pressure applying devices shown in FIGS. 1 and 6.

In addition, a back-pressure applying device 48 shown in FIG. 9 may be used. The back-pressure applying device 48 includes one or more four-port valves 50 (two valves 50 employed in the embodiment shown in FIG. 9), in place of the six-port valves 40 shown in FIG. 6. Each of the four-port valves 50 has the same structure as that of each six-port valve 40, except for the respective numbers of the ports and the channels. More specifically described, each four-port valve 50 is switchable between a first position (taken by the valve 50 that is the nearest to the column) in which the ports a, b are connected to each other and the ports c, d are connected to each other, and a second position (taken by the valve 50 that is the second nearest to the column) in which the ports a, d are connected to each other and the ports b, c are connected to each other. Therefore, the back-pressure applying device 48 can also switch the respective positions of the four-port valves 50 and thereby apply different back pressures.

Figure 10:
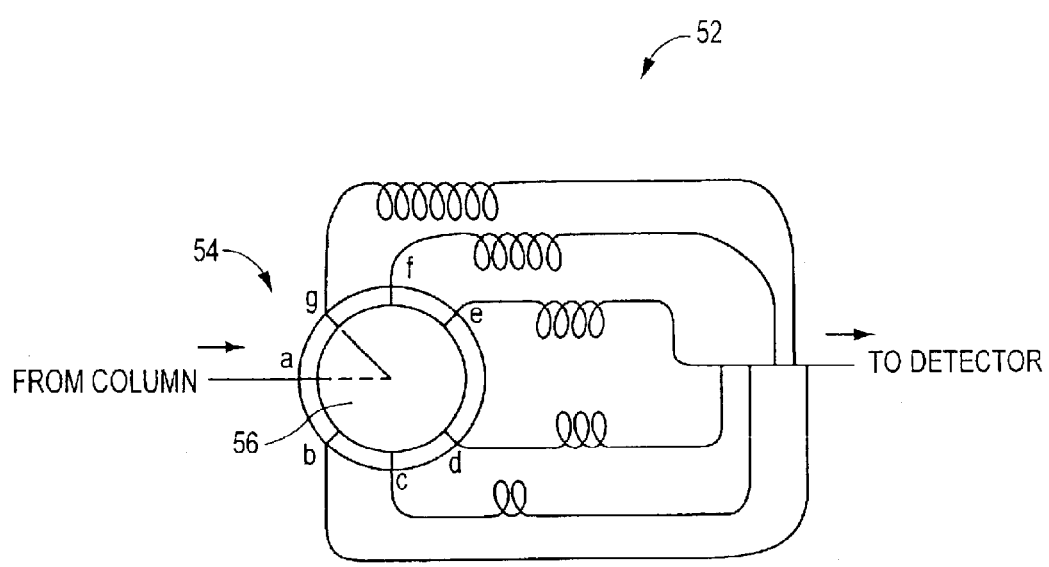
FIG. 10 is a view showing another back-pressure applying device that is different from the back-pressure applying devices shown in FIGS. 1, 6, and 9.

In addition, a back-pressure applying device 52 shown in FIG. 10 may be used. The back-pressure applying device 52 includes a rotary valve member 56, a channel-switching valve 54 that rotates the valve member 56 to cause a port, a, to communicate with an appropriate one of ports b, c, d, e, f, g, and respective pipes that are connected to the ports b, c, d, e, f, g and have different flow resistances.

The connecting pipe 24 itself may be modified to be able to function as a back-pressure applying device. More specifically described, a diameter and/or a length of the connecting pipe 24 can be adjusted to apply a back pressure to the outlet of the column 16.

Figure 11:
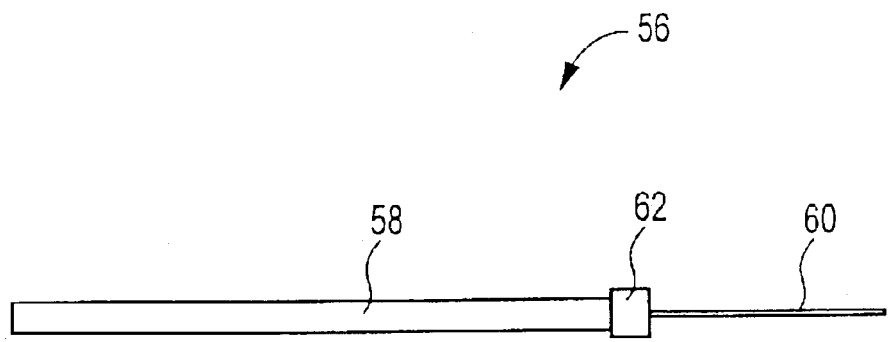
FIG. 11 is a view showing a column apparatus including a separating portion that is packed with a packing material and a thin pipe that is connected, in advance, to a downstream-side end of the separating portion.

FIG. 11 shows a column apparatus 56 including a separating portion 58 that is packed with a packing material and accordingly corresponds to a common column member; and a thin pipe 60 that is connected, in advance, to a downstream-side end of the separating portion 58. If the column apparatus 56 is used with a common liquid chromatograph apparatus, a back pressure is applied to the separating portion 58. Reference numeral 62 designates a connecting member that connects between the separating portion 58 and the pipe 60. In the conventional measurements, a pipe having an inner diameter equal to about one tenth of an inner diameter of a column is used. For example, in the case of a column having a 4.6 mm inner diameter, a pipe having a 0.50 mm inner diameter is used with the column. In contrast, the pipe 60 connected to the downstream-side end of the separating portion 58 has an inner diameter not greater than half the inner diameter of the conventional pipe, preferably not greater than one twentieth of the inner diameter of the separating portion (i.e., the column member) 58, more preferably not greater than one fortieth of the inner diameter of the same 58, and most preferably not greater than one fiftieth of the inner diameter of the same 58. According to Poiseuille's law, the back pressure applied to the separating portion 68 is proportional to the fourth power of the inner diameter of the pipe 60. Therefore, if the inner diameter of the pipe 60 is small, the short pipe 60 can apply a sufficiently high back pressure to the separating portion 58. For example, in the case where the inner diameter of the separating portion 58 is 4.6 mm and the flow rate of the mobile phase is 1.0 ml/min, if the inner diameter of the pipe 60 is 0.05 mm, a 7 cm length of the pipe 60 can apply a sufficiently high back pressure to the separating portion 58.

Figure 12:
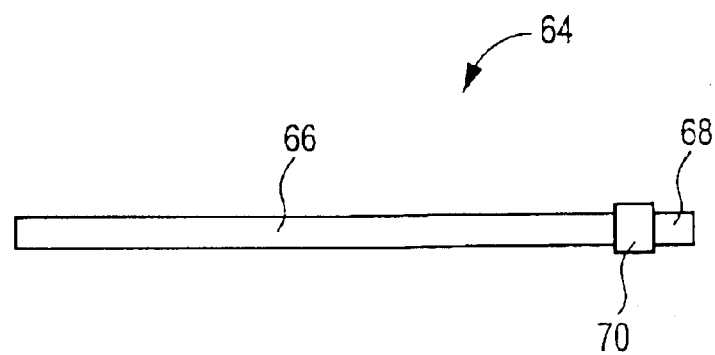
FIG. 12 is a view showing a column system including a separating column and a back-pressure applying column that is connected to a downstream-side end of the separating column.

FIG. 12 shows a column system 64 including a separating portion, i.e., a separating column 66, and a back-pressure applying column 68 that is connected to a downstream-side end of the separating column 66. In this case, the back-pressure applying column 68 can apply a back pressure to the separating column 66. Reference numeral 70 designates a connecting member that connects between the separating column 66 and the back-pressure applying column 68. If at least one of an inner diameter of the back-pressure applying column 68 and a particle diameter of a packing material of the column 68 is smaller than a corresponding one of an inner diameter of the separating column 66 and a particle diameter of a packing material of the column 66, a back pressure can be applied to the latter column 66. In the column system 64 shown in FIG. 12, the inner diameter of the back-pressure applying column 68 is equal to that of the separating column 66, and the particle diameter of the packing material, not shown, of the former column 68 is smaller than the particle diameter of the packing material of the latter column 66. For example, in the case where the inner diameter and length of the separating column 66 are 4.6 mm and 150 mm, respectively, and the particle diameter of the packing material of the same 66 is 5 $\mu$m, the inner diameter and length of the back-pressure applying column 68 may be 4.6 mm and 10 mm, respectively, and the particle diameter of the packing material of the same 68 may be 1 $\mu$m. In this case, if the mobile phase is flowed at a rate of 1.0 ml/min that is a commonly used condition, a sufficiently high back pressure can be applied to the separating column 66.

In addition, in the case where the inner diameter of the back-pressure applying column 68 is smaller than that of the separating column 66, for example, in the case where the inner diameter of the separating column 66 is 4.6 mm and the inner diameter of the back-pressure applying column 68 is 1 mm, a 10-mm length of the latter column 68 can apply, even if the respective particle diameters of the respective packing materials of the two columns 66, 68 may be equal to teach other, a sufficiently high back pressure to the former column 66, like in the case where the particle diameter of the packing material of the latter column 68 is smaller than that of the former column 66. Thus, irrespective of whether the inner diameter, or the particle size of the packing material, of the back-pressure applying column 68 is decreased, the length of the same 68 can be decreased. That is, even if the packing material that packs the back-pressure applying column 68 may be a porous material, it does not influence so much the separating function of the separating column 66. However, it is desirable to use a non-porous packing material so as not to influence the separating function.

While the present invention has been described in its preferred embodiments, it is to be understood that the present invention is by no means limited to the details of the described embodiments and may be embodied with other changes, improvements and modifications that may occur to a person skilled in the art without departing from the spirit and scope of the invention defined in the appended claims.

What is claimed is:

1. A reversed-phase liquid chromatography using a mobile phase containing water as a main component thereof, wherein the improvement comprises:

in a measurement after a flow of the mobile phase through a column is temporarily stopped and then the flow is resumed, a back pressure is applied to an outlet of the column by a back-pressure applying device which is provided between the outlet of the column and a detector.

2. A reversed-phase liquid chromatography according to claim 1, wherein the mobile phase contains 100% of water.

3. A reversed-phase liquid chromatography according to claim 1, wherein a packing material which packs the column satisfies following expressions:

$$y<1.83x+8.17 \ (1 \leq x \leq 8, y \leq 100)$$

$$y<-0.33x+25.4 \ (8 \leq x \leq 18, y \leq 100)$$

$$y<-0.93x+36.2 \ (18 \leq x \leq 30, y \leq 100)$$

where x is an alkyl-group-equivalent main-chain carbon number of a stationary phase, and y is a pore diameter (nm) of the packing material carrying the stationary phase.

4. A reversed-phase liquid chromatography according to claim 1, wherein a packing material which packs the column has, in a state in which the packing material carries the stationary phase, a not less than 10 nm diameter, and wherein an initial back pressure not lower than 15 MPa is applied to the outlet of the column when the flow is resumed.

5. A reversed-phase liquid chromatography according to claim 1, wherein a packing material which packs the column has, in a state in which the packing material carries the stationary phase, a not less than 8 nm diameter, and wherein an initial back pressure not lower than 20 MPa is applied to the outlet of the column when the flow is resumed.

6. A reversed-phase liquid chromatography using a mobile phase containing water as a main component thereof, wherein the improvement comprises:

in a measurement after a flow of the mobile phase through a column is temporarily stopped and then the flow is resumed, a back pressure not lower than 5 MPa is applied to an outlet of the column.

7. A reversed-phase liquid chromatography according to claim 6, wherein the back pressure not lower than 5 MPa is applied to the outlet of the column by a back-pressure applying device which is provided between the outlet of the column and a detector.

8. A reversed-phase liquid chromatography according to claim 6, wherein the mobile phase contains 100% of water.

9. A reversed-phase liquid chromatography according to claim 6, wherein a packing material which packs the column satisfies following expressions:

$$y<1.83x+8.17 \ (1 \leq x \leq 8, y \leq 100)$$

$$y<-0.33x+25.4 \ (8 \leq x \leq 18, y \leq 100)$$

$$y<-0.93x+36.2 \ (18 \leq x \leq 30, y \leq 100)$$

where x is an alkyl-group-equivalent main-chain carbon number of a stationary phase, and y is a pore diameter (nm) of the packing material carrying the stationary phase.

10. A reversed-phase liquid chromatography according to claim 6, wherein a packing material which packs the column has, in a state in which the packing material carries the stationary phase, a not less than 10 nm diameter, and wherein an initial back pressure not lower than 15 MPa is applied to the outlet of the column when the flow is resumed.

11. A reversed-phase liquid chromatography according to claim 6, wherein a packing material which packs the column has, in a state in which the packing material carries the stationary phase, a not less than 8 nm diameter, and wherein an initial back pressure not lower than 20 MPa is applied to the outlet of the column when the flow is resumed.

12. A reversed-phase liquid chromatography using a mobile phase containing water as a main component thereof, wherein the improvement comprises:

in a measurement after a flow of the mobile phase through a column is temporarily stopped and then the flow is resumed, an initial back pressure not lower than 5 MPa is applied to an outlet of the column when the flow is resumed; and a back pressure lower than the initial back pressure is applied to the outlet of the column after a sample is put in the column.

13. A reversed-phase liquid chromatography according to claim 12, wherein each of the initial back pressure not lower than 5 MPa and the back pressure lower than the initial back pressure is applied to the outlet of the column by a back-pressure applying device which is provided between the outlet of the column and a detector.

14. A reversed-phase liquid chromatography according to claim 12, wherein the mobile phase contains 100% of water.

15. A reversed-phase liquid chromatography according to claim 12, wherein a packing material which packs the column satisfies following expressions:

$$y<1.83x+8.17 \ (1 \leq x \leq 8, y \leq 100)$$

$$y<-0.33x+25.4 \ (8 \leq x \leq 18, y \leq 100)$$

$$y<-0.93x+36.2 \ (18 \leq x \leq 30, y \leq 100)$$

where x is an alkyl-group-equivalent main-chain carbon number of a stationary phase, and y is a pore diameter (nm) of the packing material in a state in which the packing material carries the stationary phase.

16. A reversed-phase liquid chromatography according to claim 12, wherein a packing material which packs the column has, in a state in which the packing material carries the stationary phase, a not less than 10 nm diameter, and wherein the initial back pressure not lower than 15 MPa is applied to the outlet of the column when the flow is resumed.

17. A reversed-phase liquid chromatography according to claim 12, wherein a packing material which packs the column has, in a state in which the packing material carries the stationary phase, a not smaller than 8 nm diameter, and wherein the initial back pressure not lower than 20 MPa is applied to the outlet of the column when the flow is resumed.

* * * * *